United States Patent [19]

Hamanaka

[11] Patent Number: 5,596,001

[45] Date of Patent: Jan. 21, 1997

[54] 4-ARYL-3-(HETEROARYLUREIDO)QUINOLINE DERIVATVES

[75] Inventor: Ernest S. Hamanaka, Gales Ferry, Conn.

[73] Assignee: Pfizer Inc., New York, N.Y.

[21] Appl. No.: 133,206

[22] Filed: Oct. 25, 1993

[51] Int. Cl.$^6$ ............... A61K 31/47; A61K 31/505; C07D 401/12; C07D 403/12

[52] U.S. Cl. ............... 514/313; 514/256; 514/259; 514/269; 514/309; 514/312; 514/314; 544/284; 544/298; 544/315; 544/319; 544/322; 544/328; 546/142; 546/153; 546/155; 546/159

[58] Field of Search ............... 514/243, 253, 514/256, 259, 269, 304, 310, 312, 313, 314, 315, 319; 544/183, 237, 284, 298, 299, 322, 328, 329, 315, 319, 112, 114, 116, 122, 132; 546/141, 142, 143, 153, 157, 155, 159

[56] References Cited

U.S. PATENT DOCUMENTS

| | | | |
|---|---|---|---|
| 4,623,662 | 11/1986 | DeVries | 514/596 |
| 4,716,175 | 12/1987 | Hoefle et al. | 514/357 |
| 4,743,605 | 5/1988 | Hoefle et al. | 514/269 |
| 5,254,565 | 10/1993 | Meguro et al. | 514/312 |

FOREIGN PATENT DOCUMENTS

| 0009017 | 6/1991 | WIPO | 546/159 |
|---|---|---|---|

OTHER PUBLICATIONS

Schaefer et al. CA 80: 3361f, p. 294, 1974.

*Primary Examiner*—Yogendra N. Gupta
*Attorney, Agent, or Firm*—Peter C. Richardson; Paul H. Ginsburg; Seymour G. Bekelnitzky

[57] ABSTRACT

Compounds of the formula

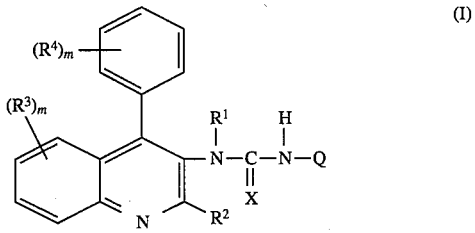

(I)

and the pharmaceutically acceptable salts thereof, wherein $R^1$, $R^2$, $R^3$, $R^4$, m, X and Q are as defined below, and novel intermediates used in the synthesis of such compounds. The compounds of formula I are inhibitors of acyl coenzyme A: cholesterol acyltransferase (ACAT) and are useful as hypolipidemic and natiatherosclerosis agents.

11 Claims, No Drawings

4-ARYL-3-(HETEROARYLUREIDO)QUINOLINE DERIVATVES

BACKGROUND OF THE INVENTION

The present invention relates to new 4-aryl-3-(heteroarylureido)quinoline derivatives, pharmaceutical compositions comprising such compounds, novel 3-nitroquinoline intermediates used in the synthesis of such compounds and the use of such compounds to inhibit intestinal absorption of cholesterol, lower serum cholesterol and reverse the development of atherosclerosis. The compounds are inhibitors of acyl coenzyme A: cholesterol acyltransferase (ACAT).

Cholesterol that is consumed in the diet (dietary cholesterol) is absorbed as free cholesterol by the mucosal cells of the small intestine. It is then esterified by the enzyme ACAT, packaged into particles known as chylomicrons, and released into the bloodstream. Chylomicrons are particles into which dietary cholesterol is packaged and transported in the bloodstream. By inhibiting the action of ACAT, the compounds of this invention prevent intestinal absorption of dietary cholesterol and thus lower serum cholesterol levels. They are therefore useful in preventing atherosclerosis, heart attacks and strokes.

By inhibiting the action of ACAT, the compounds of the present invention also enable cholesterol to be removed from the walls of blood vessels. This activity renders such compounds useful in slowing or reversing the development of atherosclerosis as well as in preventing heart attacks and strokes.

Other inhibitors of ACAT are referred to in U.S. Pat. Nos. 4,716,175 and 4,743,605 (a divisional of the '175 patent), the European Patent Applications having publication numbers 0 242 610, 0 245 687, 0 252 524, and 0 354 994, and U.S. patent application 07/648,677, filed Jan. 31, 1991 and assigned in common with the present application.

Certain ureas and thioureas as antiatherosclerosis agents are referred to in U.S. Pat. No. 4,623,662 and in the European Patent Applications having publication numbers 0 335 374, 0 386 487, 0 370 740, 0 405 233 and 0 421 456.

SUMMARY OF THE INVENTION

The present invention relates to compounds of the formula

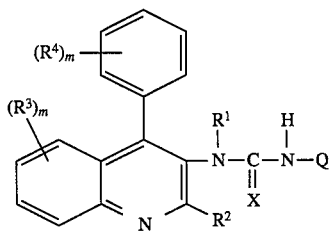

(I)

wherein each m is independently selected from 0 to 4;

$R^1$ is selected from hydrogen, $(C_1-C_6)$ alkyl, $(C_6-C_{12})$ aralkyl wherein the aryl moiety is selected from phenyl, thienyl, furyl, and pyridinyl;

$R^2$ is selected from hydrogen, $(C_1-C_6)$ alkyl and $(C_1-C_6)$ alkoxy;

Each $R^3$ and $R^4$ is independently selected from hydrogen, halogen, $(C_1-C_6)$ alkyl optionally substituted with one or more halogen atoms, $(C_1-C_6)$ alkoxy optionally substituted with one or more halogen atoms, $(C_1-C_6)$ alkylthio optionally substituted with one or more halogen atoms, nitro, carboxyl optionally esterified with a $(C_1-C_6)$ alkyl group, hydroxyl, $(C_1-C_6)$ acyloxy and $NR^{12}R^{13}$ wherein $R^{12}$ and $R^{13}$ are the same or different and are selected from the group consisting of hydrogen, $(C_1-C_6)$alkyl, optionally halogenated $(C_1-C_6)$acyl, optionally halogenated $(C_1-C_6)$alkylsulfonyl, $(C_1-C_6)$alkylaminocarbonyl and $(C_1-C_6)$alkoxycarbonyl, or $R^{12}$ and $R^{13}$, together with the nitrogen to which they are attached, form a piperidine, pyrrolidine or morpholine ring;

X is sulfur or oxygen; and

Q is a group of the formula

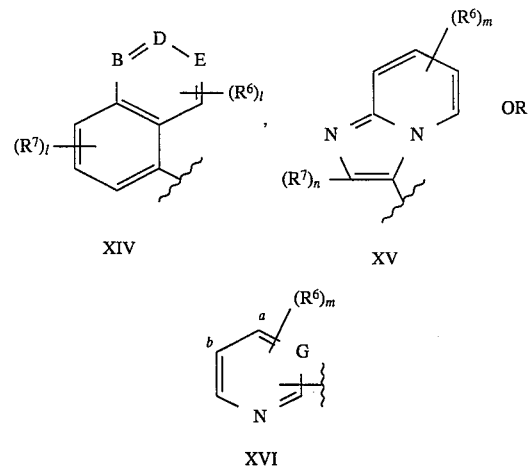

wherein m is as defined above;

n is 0 or 1.

Each l is independently selected from 0 to 3;

Each $R^6$ and $R^7$ is independently selected from the group consisting of halogen, $(C_1-C_6)$alkyl, $(C_1-C_6)$ haloalkyl, optionally halogenated $(C_1-C_6)$ alkoxy, optionally halogenated $(C_1-C_6)$ alkylthio, $(C_5-C_7)$ cycloalkylthio, phenyl $(C_1-C_6)$ alkylthio, substituted phenylthio, heteroarylthio, heteroaryloxy, $(C_1-C_6)$ alkylsulfinyl, $(C_1-C_6)$ alkylsulfonyl, $(C_5-C_7)$ cycloalkylsulfinyl, $(C_5-C_7)$ cycloalkylsulfonyl, phenyl $(C_1-C_6)$ alkylsulfinyl, phenyl $(C_1-C_6)$ alkylsulfonyl, substituted phenylsulfinyl, substituted phenylsulfonyl, heteroarylsulfinyl, heteroarylsulfonyl, and $NR^{10}R^{11}$, wherein $R^{10}$ and $R^{11}$ are the same or different and are selected from the group consisting of hydrogen, $(C_1-C_6)$ alkyl, phenyl, substituted phenyl, $(C_6-C_6)$ acyl, aroyl, and substituted aroyl, wherein said substituted phenyl and substituted aroyl groups are substituted with one or more substituents independently selected from the group consisting of $(C_1-C_6)$ alkyl, $(C_1-C_6)$ alkoxy, $(C_1-C_6)$ alkylthio, halogen and trifluoromethyl or $R^{10}$ and $R^{11}$, together with the nitrogen to which they are attached, form a piperidine, pyrrolidine or morpholine ring; and B, D, E and G are selected from the group consisting of nitrogen and carbon, with the proviso that one or more of B, D and E is nitrogen, and with the proviso that when G is nitrogen, the group XVI is attached to the nitrogen of formula I at the 4 or 5 position of the pyrimidine ring (designated by a and b) wherein any of said nitrogens may be oxidized;

or a pharmaceutically acceptable salt of such compound.

Unless otherwise indicated, the term "halogen", as used herein, includes fluoro, chloro, bromo and iodo.

Unless otherwise indicated, the term "alkyl", as used herein, may be straight, branched or cyclic, and may include straight and cyclic moieties as well as branched and cyclic moieties.

Unless otherwise indicated, the term "one or more substituents" or "one or more halogen atoms", as used herein, refers to from one to the maximum number of substituents possible based on the number of available bonding sites.

The present invention also relates to compounds of the formula

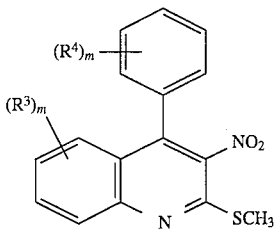

wherein m, $R^3$ and $R^4$ are as defined above with the proviso that no $R^3$ or $R^4$ is an optionally substituted alkylthio group. These compounds are useful as intermediates in the synthesis of compounds of the formula I.

Preferred compounds of formula I are those wherein Q is 6-($C_1$–$C_3$)alkoxyquinolin-5-yl, 6-($C_1$–$C_3$)alkylthioquinolin-5-yl, 6-($C_1$–$C_3$)alkylquinolin-5-yl, 6-($C_1$–$C_3$)alkylthioisoquinolin-5-yl, 6-($C_1$–$C_3$)alkoxyisoquinolin-5-yl, 4,6-bis[($C_1$–$C_3$)alkylthio]-2-methylpyrimidin-5-yl, 4,6-bis [($C_1$–$C_3$)alkylthio]pyrimidin-5-yl, 2,4-bis[($C_1$–$C_3$)alkylthio]-6-methylpyridin-3-yl or 2,4-bis[($C_1$–$C_3$)alkylthio]pyridin-3-yl.

Other preferred compounds of the formula I are those wherein $R^1$ is hydrogen and $R^2$ is selected from hydrogen and methoxy and each $R^3$ and $R^4$ is selected from ($C_1$–$C_6$)alkyl, chlorine, fluorine and trifluoromethyl.

More preferred compounds of the formula I are those wherein Q is 6-methoxyquinolin-5-yl, 6-methylthioquinolin-5-yl, 6-methoxyisoquinolin-5-yl, 6-methylthioisoquinolin-5-yl, 2-methyl-4,6-bis(methylthio)pyrimidin-5-yl, 6-methyl-2,4-bis(methylthio)pyridin-3-yl, 2,4-bis(ethylthio)pyridin-3-yl, 2,4,6-trimethylpyridin-3-yl, 2,4-dimethoxy-6-methylpyridin-3-yl, 6-(4-methoxyphenylthio)-quinolin-5-yl and 6-pentylthioquinolin-5-yl.

Specific preferred compounds of formula I include:
3-[3-{4,6-Bis(methylthio)-2-methylpyrimidin-5-yl }ureido]-6-chloro-4-(2-chlorophenyl)quinoline;
3-[3-{2,4-Bis(methylthio)-6-methylpyridin-3-yl}ureido]-6-chloro-4-(2-chlorophenyl)quinoline;
6-Chloro-4-(2-chlorophenyl)-3-[3-(6-methylthioquinolin-5-yl)ureido]quinoline;
3-[3-{2,4-Bis(methylthio)-6-methylpyridin-3-yl}ureido]-4-(2-chlorophenyl)-6-methylquinoline;
3-[3-{4,6-Bis(methylthio)-2-methylpyrimidin-5-yl}ureido]-4-(2-chlorophenyl)-6-methylquinoline;
3-[3-{4,6-Bis(methylthio)-2-methylpyrimidin-5-yl}ureido]-4-(2-chlorophenyl)-6-ethylquinoline;
3-[3-{2,4-Bis(methylthio)-6-methylpyridin-3-yl}ureido]-4-(2-chlorophenyl)-6-ethylquinoline;
4-(2-Chlorophenyl)-6-methyl-3-[3-(6-methylthioquinolin-5-yl)ureido]quinoline;
4-(2-Chlorophenyl)-6-ethyl-3-[3-(6-methylthioquinolin-5-yl)ureido]quinoline;
3-[3-{2,4-Bis(methylthio)-6-methylpyridin-3-yl}ureido]-4-(2-chlorophenyl)-6-isopropylquinoline;
3-[3-{4,6-Bis(methylthio)-2-methylpyrimidin-5-yl}ureido]-4-(2-chlorophenyl)-6-isopropylquinoline;
4-(2-Chlorophenyl)-6-isopropyl-3-[3-(6-methylthioquinolin-5-yl)ureido]quinoline; and 3-[3-{2,4-Bis(methylthio)-6-methylpyridin-3-yl}ureido]-4-(2-chlorophenyl)-6,8-dimethylquinoline.
4-(2-Chlorophenyl)-6-isopropyl-3-[3-(2,4,6-trimethylpyridin-3-yl)ureido]quinoline;
4-(2-Chlorophenyl)-6-isopropyl-3-[3-(2,4-dimethoxy-6-methylpyridin-3-yl)ureido]quinoline;
4-(2-Chlorophenyl)-6-methyl-3-[3-(6-methoxyquinolin-5-yl)ureido]quinoline;
6-Chloro-4-(2-chlorophenyl)-3-[3-(6-methoxyquinolin-5-yl)ureido]quinoline;
6-Chloro-4-(2-chlorophenyl)-3-[3-{6-(4-methoxyphenylthio)quinolin-5-yl}ureido]quinoline;
6-Chloro-4-(2-chlorophenyl)-3-[3-(6-pentylthioquinolin-5-yl)ureido]quinoline;
3-[3-{2,4-Bis(methylthio)-6-methylpyridin-3-yl}ureido]-6-chloro-4-(2-chlorophenyl)-2-methoxyquinoline;
6-Chloro-4-(2-chlorophenyl)-2-methoxy-3-[3-(6-methylthioquinolin-5-yl)ureido]quinoline.

Other compounds of the formula I include:
6-Chloro-4-(2-chlorophenyl)-3-[3-(6-methylquinolin-5-yl)ureido]quinoline;
6-Chloro-4-(2-chlorophenyl)-3-[3-(2,4-diethoxy-6-methylpyridin-3-yl)ureido]quinoline;
3-[3-{2,4-Bis(isopropylthio)-6-methylpyridin-3-yl}ureido]-6-chloro-4-(2-chlorophenyl)quinoline;
3-[3-{4,6-Bis(ethylthio)pyrimidin-5-yl}ureido]-6-chloro-4-(2-methylphenyl)quinoline;
6-Chloro-4-(2-chlorophenyl)-3-[3-(2-dimethylamino-6-methyl-4-methylthiopyridin-3-yl)ureido]quinoline;
3-[3-{2,4-Bis(ethylthio)pyridin-3-yl}ureido]-6-chloro-4-(2-fluorophenyl)quinoline;
3-[3-{4,6-Bis(methylthio)-2-methylpyrimidin-5yl}ureido]-6-chloro-4-(2-methylphenyl)quinoline;
3-[3-{2,4-Bis(methylthio)-6-methylpyridin-3-yl}ureido]-6-chloro-4-(2-chlorophenyl)-8-methylquinoline;
3-[3-{2,4-Bis(methylthio)pyridin-3-yl}ureido]-4-(2-chlorophenyl)-6-fluoroquinoline;
3-[3-{2,4-Bis(methylthio)-6-methylpyridin-3-yl}ureido]-6-chloro-4-(3,4-dimethoxyphenyl)quinoline;
3-[3-{2,4-Bis(methylthio)-6-methylpyridin-3-yl}ureido]-6-difluoromethylthio-4-phenylquinoline;
3-[3-{4,6-Bis(methylthio)-2-methylpyrimidin-5yl}ureido]-6-difluoromethoxy-4-phenylquinoline;
3-[3-{2,4-Bis(ethylthio)pyridin-3-yl}ureido]-8-chloro-4-(2-chlorophenyl)-6-methylquinoline;
3-[3-{2,4-Bis(methylthio)pyridin-3-yl}ureido]-6-chloro-4-(2,3,4-trimethoxyphenyl)quinoline;
3-[3-{4,6-Bis(ethylthio)-2-methylpyrimidin-5yl}ureido]-6-chloro-4-(2-methoxyphenyl)quinoline;
3-[3-{2,4-Bis(methylthio)-6-methylpyridin-3-yl}ureido]-4-(2-chlorophenyl)-6,7-dimethylquinoline;
3-[3-{4,6-Bis(methylthio)pyrimidin-5-yl}ureido]4-(2-chlorophenyl)-5,6,7-trimethylquinoline; and
3-[3-{2,4-Bis(methylthio)-6-methylpyridin-3-yl}ureido]-4-(2-chlorophenyl)-6-dimethylaminoquinoline.

The present invention also relates to all radiolabelled forms of the compounds of the formulae I and II, including those comprising tritium and/or carbon-14 ($^{14}C$). Such radiolabelled compounds are useful as research and diagnostic tools in metabolism pharmacokinetic studies and in binding assays in both animals and man.

The present invention also relates to a pharmaceutical composition for inhibiting ACAT, inhibiting intestinal absorption of cholesterol, reversing or slowing the development of atherosclerosis, or lowering the concentration of serum cholesterol in a mammal, including a human, comprising an amount of a compound of the formula I, or a pharmaceutically acceptable salt thereof, effective in inhibiting ACAT, inhibiting intestinal absorption of cholesterol, reversing or slowing the development of atherosclerosis, or lowering the concentration of serum cholesterol, and a pharmaceutically acceptable carrier.

The present invention also relates to a method for inhibiting ACAT, inhibiting intestinal absorption of cholesterol, reversing or slowing the development of atherosclerosis, or lowering the concentration of serum cholesterol in a mammal, including a human, comprising administering to a mammal an amount of a compound of the formula I, or a pharmaceutically acceptable salt thereof, effective in inhibiting ACAT, inhibiting intestinal absorption of cholesterol, reversing or slowing the development of atherosclerosis, or lowering the concentration of serum cholesterol.

Examples of pharmaceutically acceptable acid addition salts of the compounds of formula I are the salts of hydrochloric acid, p-toluenesulfonic acid, fumaric acid, citric acid, succinic acid, salicyclic acid, oxalic acid, hydrobromic acid, phosphoric acid, methanesulfonic acid, tartaric acid, di-p-toluoyl tartaric acid, and mandelic acid.

DETAILED DESCRIPTION OF THE INVENTION

Reaction schemes 1–3 below illustrate the synthesis of the compounds of this invention. Except where otherwise stated, $R^1, R^2, R^3, R^4, R^6, R^7, R^{10}, R^{11}, R^{12}, R^{13}$, Q, X, B, D, E, G, l, m and n in the reaction schemes and discussion that follows are defined as above.

SCHEME 1

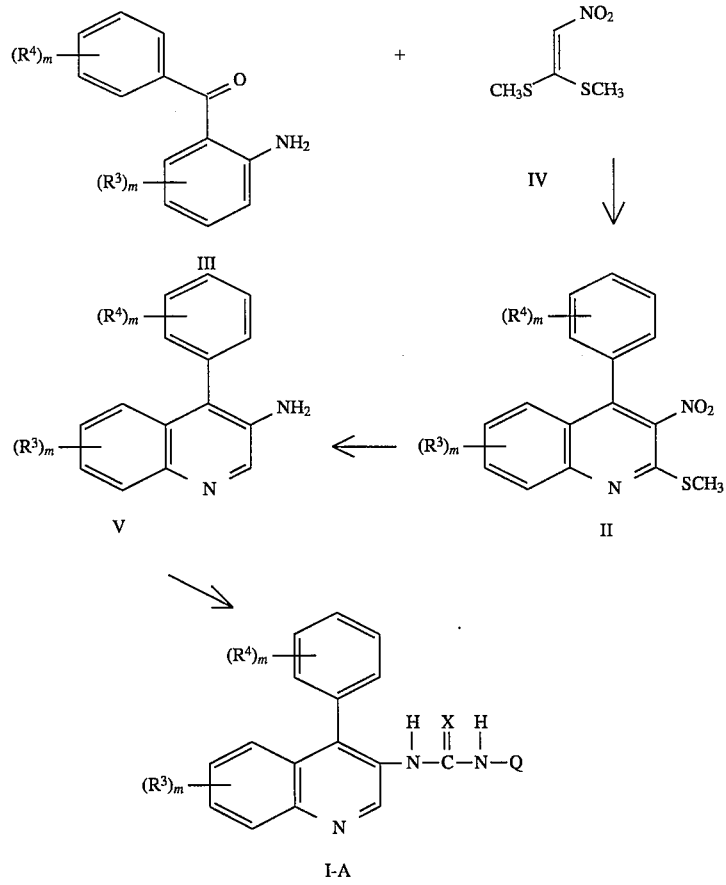

[$R^1$ = hydrogen]

SCHEME 2
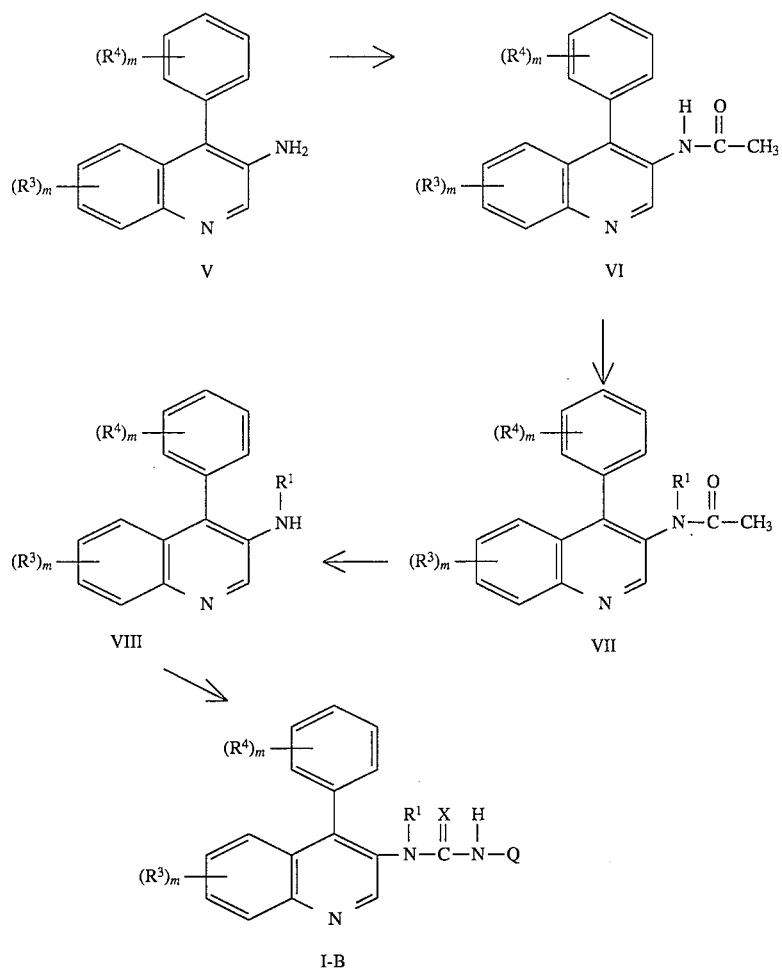
[R¹ is other than hydrogen]

SCHEME 3

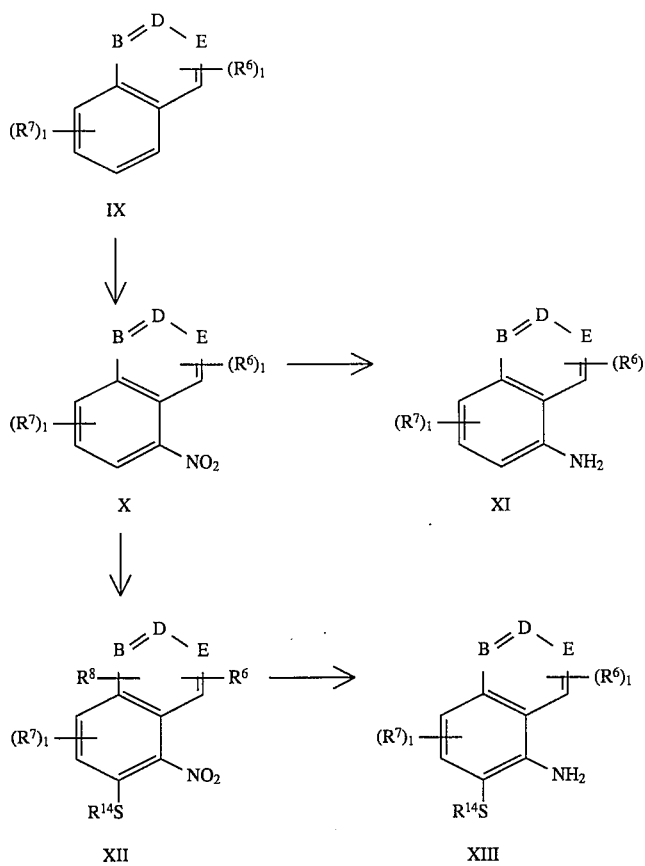

Scheme 1 illustrates the preparation of compounds of the formula I wherein $R^1$ is hydrogen. Referring to scheme 1, the starting material of formula III, which may be prepared by procedures referred to in *Synthesis*, 677 (1980), is reacted with 1,1-bis(methylthio)-2-nitroethylene (IV) to produce the corresponding compound of formula II. This reaction is generally carried out in an inert solvent such as acetic acid, propionic acid or polyphosphoric acid at a temperature from about 100° C. to about 160° C. for about 2 to 24 hours. It is preferably carried out in acetic acid at about 120° C. for about 16 hours.

The compound of formula II formed in the foregoing reaction is then reduced to form the corresponding compound of formula V. Typically, the reduction and desulfurization is carried out in one step using an excess of Raney nickel in a suitable inert solvent such as ethanol, methanol, dioxane, acetone, tetrahydrofuran or dimethylformamide, with or without the addition of water. This reaction is usually carried out for about 1 to 8 hours. The reaction temperature may range from about 20° C. to about 100° C. Preferably, the compound of formula II is reduced and desulfurized in the presence of excess Raney nickel in ethanol at about 80° C. for about 2 to 3 hours.

Alternatively, the compound of formula V may be prepared from the corresponding compound of formula II in a two step procedure wherein the compound of formula II is first reduced to the corresponding amino derivative which is then, in the second step, desulfurized to the compound of formula V. Suitable reducing agents for the first step include stannous chloride, titanium (III) chloride, iron or zinc, with or without an acid catalyst (e.g., hydrochloric or acetic acid), or hydrogen gas with an appropriate catalyst, for about 2 to 16 hours at a temperature of about 0° C. to about 100° C. In the second step, the desulfurization is carried out using an excess of Raney nickel as described above.

The reductive desulfurization of compounds of the formula II may also be carried out using a copper-aluminum alloy as described in *Helv. Chem. Acta.* 71, 531 (1988) or using nickel boride as described in *J. Chem. Soc. Chem. Commun.*, 819 (1990) and *J. Chem. Soc. (c)* 1122 (1968).

Alternative synthetic methods of preparing compounds of the formula V are described in EP 0354994A2.

The preparation of compounds of the formulae II and V wherein $R^3$ and $R^4$ are hydrogen and the same compounds wherein $R^3$ and $R^4$ are hydrogen except for one $R^3$ which is 6-chloro are described in *Z. Chem.*, 8, 294 (1973) and in *J. prakt. Chem.*, 318, 39, (1976).

Treatment of the compound of formula V so formed with a compound of the formula QN=C=X yields the corresponding urea (X=O) or thiourea (X=S) of the formula I-A. Procedures for the preparation of compounds of the formula QN=C=X are known in the literature and several methods are reviewed in "Organic Functional Group Preparations Vol 1", Chapter 12, Academic Press, New York (1968). The preparation of ureas and thioureas by the reaction of amines with isocyanates and isothiocyanates, respectively, are reviewed in "Organic Functional Group Preparations, Vol. 2", Chapter 6, Academic Press, New York (1971).

Compounds of the formula QN=C=O may be obtained by reacting compound of the formula $QNH_2$ with 1 to 6 equivalents of an appropriate reagent such as phosgene, trichloromethyl chloroformate or bis(trichloromethyl)carbonate. The reaction is generally carried out in an inert ether, aromatic hydrocarbon or chlorinated hydrocarbon solvent such as dioxane, diisopropyl ether, benzene, toluene, dichloromethane or chloroform. It may be conducted in the presence of a base such as a tertiary amine (e.g., pyridine, triethylamine or quinoline). Reaction temperatures may range from about 0° C. to about 120° C., and are preferably from about 20° C. to about 100° C. Preferably, the heterocyclic amine of formula $QNH_2$ is reacted with 1 to 2 equivalents of trichloromethyl chloroformate in refluxing dichloromethane for about 18 hours.

The reaction of compounds of the formula $QN=C=X$ with compounds of formula V to form compounds of the formula I-A is carried out in an inert, anhydrous solvent such as chloroform, benzene, dimethylformamide, dioxane or tetrahydrofuran, at a temperature from about 20° C. to 100° C., for about 3 to 30 hours, preferably in dimethylformamide at about 80° C. for about 16 hours.

Alternatively, compounds having the formula I-A may be prepared by reacting the intermediate of formula $QNH_2$ with the appropriate quinolin-3-yl isocyanate which may be prepared by methods described in EP 0354994A2. This reaction is typically carried out under conditions similar to those described above for the reaction of compounds of the formula V with compounds of the formula $QN=C=X$.

Compounds of the formula I wherein $R^1$ is other than hydrogen may be prepared by the procedure described below and illustrated in scheme 2.

Referring to scheme 2, the appropriate starting material of the formula V is acylated to form the corresponding compound of formula VI according to the method set forth in U.S. Pat. No. 3,798,226, which is incorporated herein by reference.

The $R^1$ substituent is added to the compound of formula VI by reacting it with a compound of the formula $R^1Z$ wherein Z is a leaving group. Appropriate leaving groups include halogen, ($C_1$–$C_6$) alkanesulfonyloxy groups (e.g., methanesulfonyloxy, ethanesulfonyloxy, etc.) and ($C_6$–$C_{10}$) arylsulfonyloxy groups (e.g., benzenesulfonyloxy, p-toluenesulfonyloxy, etc.). Suitable solvents for this reaction include inert solvents such as tetrahydrofuran (THF), dimethoxyethane (DME), and N,N-dimethylformamide. The reaction is accelerated in the presence of a base such as sodiumhydride, sodium methylate, sodium ethylate, sodium amide or potassium t-butoxide. The reaction is usually carried out at a temperature from about 20° C. to about 120° C., and is preferably carried out at a temperature about 0° C. to about 100° C. The preferred solvent is dimethylformamide and the preferred base is sodium hydride.

Hydrolysis of the resulting amide of formula VII yields the corresponding amine of formula VIII. The hydrolysis reaction is usually conducted in a protic solvent such as a lower alcohol (e.g. methanol, ethanol, or propanol) or acetic acid. It is preferably conducted in the presence of a mineral acid (e.g. hydrochloric acid, hydrobromic acid or sulfuric acid) in an amount of about 2 to 20 moles (preferably about 3 to 15 moles) per mole of compound of formula VII. The reaction temperature may range from about 60° C. to about 120° C. It is preferably between about 70° C. and 100° C.

Alternatively, compounds of the formula VIII wherein $R^1$ is other than hydrogen may be prepared by acylating the corresponding compound of formula V with an appropriate acylating agent such as $R^{15}COCl$ or $[R^{15}CO]_2O$, wherein $R^{15}$ is the same as $R^1$ except that it contains one less methylene group than $R^1$, according to the method described in U.S. Pat. No. 3,798,226, and then reducing the resulting amide to the desired compound of formula VIII using an appropriate reducing agent such as lithium aluminum hydride, sodium bis(2-methoxyethoxy)aluminum hydride or diborane. The reduction is generally carried out in an inert solvent such as tetrahydrofuran, dioxane or dimethoxyethane at a temperature from about 25° C. to about 110° C.

The compound of formula VIII may be converted into the desired corresponding compound of formula I-B by the method described above and illustrated in scheme 1 for preparing compounds of the formula I-A from compounds of the formula V.

The aminopyrimidine and aminopyridine intermediates (i.e., compounds of the formula Q—$NH_2$) used in the present invention are known in the literature or may be prepared by methods known in the art from various pyrimidine and pyridine intermediates that are known in the literature or commercially available. The pyrimidine and pyridine intermediates that are commercially available include 4,6-dichloro-5-nitropyrimidine, 2,4-dihydroxy-6-methylpyrimidine, 4,6-dihydroxy-2-methylpyrimidine, 5-nitrobarbituric acid, 2-hydroxy-4-methyl-3-nitropyridine and 2,3-dihydroxypyridine. References for the preparation of many of the pyrimidine and pyridine intermediates can be found in the monographs "The Pyrimidines", ed by D. J. Brown (1962) and "Pyridine and its Derivatives", ed. by R. A. Abramovitch (1961), Interscience Publishers, Inc., New York, N.Y., and their Supplements. The foregoing pyridine and pyrimidine compounds may be converted to the corresponding aminopyridine and aminopyrimidine intermediates useful in the synthesis of the compounds of this invention by methods well known to those skilled in the art. (See "The Pyrimidines", ed. by D. J. Brown (1962) and "Pyridine and its Derivatives", ed. by R. A. Abramovitch (1961), Interscience Publishers, Inc., New York, N.Y., and their Supplements).

The preparation of certain aminopyridine and aminopyrimidine intermediates is described in greater detail below.

4,6-Disubstituted-5-aminopyrimidine derivatives may be prepared by reacting the appropriately substituted 4,6-dihydroxypyrimidine with a nitrating agent such as fuming nitric acid in acetic acid at a temperature from about 15° C. to about 40° C. for a period of about 1 to about 5 hours. The resulting 5-nitropyrimidines may be converted to the 4,6-dichloro-5-nitropyrimidine intermediates using a chlorinating agent such as phosphoryl chloride, alone or in the presence of a base, preferably diethylaniline, at a temperature from about 100° to about 115° C. for a period of about 0.5 to about 2 hours. Procedures for carrying out these transformations are described in *J. Chem. Soc.*, 3832 (1954).

4,6-bis(alkylthio)-5-nitropyrimidine derivatives may be prepared by reacting the appropriate dichloro intermediate with two equivalents of sodium alkylthiolate in a solvent such as dimethylformamide or methanol, preferably methanol, for about 4 to about 16 hours at a temperature from about 0° C. to about 30° C., preferably at ambient temperature.

Monosubstitution of the 4,6-dichloro-5-nitropyrimidine intermediates is accomplished by reacting them with one equivalent of nucleophile at a reaction temperature from about 0° C. to about 100° C. (depending on the reactivity of the nucleophile) in an inert solvent such as dimethylformamide or tetrahydrofuran for a period of about 4 to about 16 hours. The resulting monochloro derivative is then reacted with one equivalent of a different nucleophile to yield a disubstituted derivative with different substitutents on the carbon atoms at positions 4 and 6 of the pyrimidine ring. Reduction of the 4,6-disubstituted-5-nitropyrimidines using a reducing agent such as stannous chloride in concentrated hydrochloric acid or hydrogen gas with an appropriate catalyst yields the corresponding 5-aminopyrimidine derivatives.

2,4-Disubstituted-3-aminopyridine derivatives may be prepared by reacting the appropriate 2,4-dihydroxypyridines with a nitrating agent such as concentrated nitric acid at a temperature from about 80° C. to about 100° C. for about 15 to 60 minutes. (For example, the preparation of 2,4-dihydroxy-6-methyl-3-nitropyridine is described in *J. Heterocyclic Chem.*, 1970, 7, 389). The resulting 2,4-dihydroxy-3-nitro-pyridines are sequentially converted to the 2,4-dichloro-3-nitropyridines, 2,4-disubstituted-3-nitropyridines and 2,4-disubstituted-3-aminopyridines using reaction conditions similar to those described above for the pyrimidine series.

In a similar manner, appropriately substituted monohydroxypyrimidines and pyridines may be converted sequentially to nitro monohydroxy derivatives and nitro monochloro derivatives. The nitro monochloro intermediates are then reacted with the appropriate sulfur, oxygen or nitrogen nucleophiles to yield oxygen, sulfur or nitrogen substituted nitro derivatives which may be reduced to the desired aminopyrimidines or pyridines.

The synthesis of certain 5-aminoquinolines and 5-aminoisoquinolines used as reactants in schemes 1 and 2 are illustrated in scheme 3. Referring to scheme 3, 5-aminoquinolines and isoquinolines of the formulae XV and XVII may be prepared as follows. A quinoline or isoquinoline of the formula IX is nitrated at the 5 position, respectively, by reacting it with a nitrating agent such as nitric acid or potassium nitrate with or without an acid catalyst such as sulfuric acid, for from about 2 to 16 hours at a temperature from about 0°–100° C. The nitro compound of formula X so formed is then reduced using a reducing agent such as stannous chloride, iron, zinc, or hydrogen gas with an appropriate catalyst, with or without an acid catalyst such as hydrochloric acid, for from about 2 to 16 hours at a temperature from about 0°–100° C., to yield the corresponding 5-aminoquinoline or 5-aminoisoquinoline of formula XI.

Compounds of the formula XIII, wherein B or D is nitrogen and wherein $R^{14}$ is $(C_1-C_6)$ alkyl, $(C_5-C_7)$ cycloalkyl, phenyl $(C_1-C_4)$ alkyl, phenyl, substituted phenyl, heteroaryl, or substituted heteroaryl, may be prepared as follows. A compound of the formula X, wherein 1 is at least one and one $R^7$ is —Cl, which is attached to the quinoline or the isoquinoline ring at the 6 position, is reacted with a compound of the formula $R^{14}SH$, wherein $R^{14}$ is as defined above, and a base such as sodium hydride, or such compound of the formula X is reacted with a compound of the formula $R^{14}SNa$, wherein $R^{14}$ is as defined above, in an inert solvent such as tetrahydrofuran, for about 4 to 16 hours at a temperature of from about −10° C. to room temperature. The preferred temperature is −10° C. This reaction yields a compound of the formula XII, which is then converted to the corresponding 5-aminoquinoline or isoquinoline of the formula XIII by the method described above for reduction of compounds of formula X.

Except where otherwise noted, pressure is not critical in any of the above reactions. Preferred temperatures for the above reactions were stated where known. In general, the preferred temperature for each reaction is the lowest temperature at which product will be formed. The preferred temperature for a particular reaction may be determined by monitoring the reaction using thin layer chromatography.

2-Substituted-5-aminoquinolines used in the preparation of compounds of formula I wherein $R^2$ is other than hydrogen are prepared by the method of Ikeda (EP 0 421 456). They are then used, in lieu of the compounds of formulae V and VIII in schemes 1 and 2, respectively, to form the 2-substituted compounds of formula I wherein $R^1$ is hydrogen or other than hydrogen, respectively.

The novel compounds of formula I and the pharmaceutically acceptable salts thereof are useful as inhibitors of acyl coenzyme A: cholesterol acyltransferase (ACAT). As such they inhibit intestinal absorption of cholesterol in mammals and are useful in the treatment of high serum cholesterol in mammals, including humans. As used herein, treatment is meant to include both the prevention and alleviation of high serum cholesterol. The compound may be administered to a subject in need of treatment by a variety of conventional routes of administration, including orally, parenterally and topically. In general, these compounds will be administered orally or parenterally at dosages between about 0.5 and about 30 mg/kg body weight of the subject to be treated per day, preferably from about 0.8 to 5 mg/kg. For an adult human of approximately 70 kg of body weight, the usual dosage would, therefore, be about 3.5 to about 2000 mg per day. However, some variation in dosage will necessarily occur depending on the condition of the subject being treated and the activity of the compound being employed. The person responsible for administration will, in any event, determine the appropriate dose for the individual subject.

A compound of formula I or a pharmaceutically acceptable salt thereof may be administered alone or in combination with pharmaceutically acceptable carriers, in either single or multiple doses. Suitable pharmaceutical carriers include inert solid diluents or fillers, sterile aqueous solution and various organic solvents. The resulting pharmaceutical compositions are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of a compound of formula I or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. Such solutions are especially suitable for intravenous, intramuscular, subcutaneous and intraperitioneal administration. In this connection, the sterile aqueous media employed are all readily available by standard techniques known to those skilled in the art.

The activity of the compounds of the present invention as ACAT inhibitors may be determined by a number of standard biological or pharmacological tests. For example, the following procedure was used to determine the ACAT inhibiting activity of compounds of formula I. ACAT was assayed in microsomes isolated from chow fed Sprague-Dawley rats according to Bilheimer, J. T., Meth. Enzymol., 111, ps 286–293 (1985), with minor modifications. Microsomes from rat liver were prepared by differential centrifugation and washed with assay buffer prior to use. The assay mixture contained 25 ul of BSA (40 mg/ml), 30 ul of rat liver microsome solution (100 ug microsomal protein), 20 ul of assay buffer (0.1M $K_2PO_4$, 1.0 mM reduced Glutathione, pH 7.4), 20 ug of cholesterol in 100 ul of a 0.6% Triton WR-1339 solution in assay buffer, and 5 ul of test compound dissolved in 100% DMSO (total volume=180 ul). The assay mixture was incubated for 30 min at 37° C. The reaction was started by the addition of 20 ul of $14°$ C.-Oleoyl-CoA (1000 uM, 2,000 dpm/nmol) and run for 15 min at 37° C. The reaction was stopped by the addition of 1 ml ETOH. The lipids were extracted into 4 ml hexane. A 3 ml aliquot was dried under $N_2$, and resuspended in 100 ul of chloroform. 50 ul of chloroform were spotted on a heat activated TLC plate and developed in hexane: diethyl ether: acetic acid (85:15:1, v:v:v). Incorporation of radioactivity into cholesteryl esters was quantified on a Berthold LB2842 Linear TLC Analyzer. ACAT inhibition was calculated relative to a DMSO control assay.

The activity of the compounds of formula I in inhibiting intestinal absorption of cholesterol may be determined by the procedure of Melchoir and Harwell, *J. Lipid. Res.*, 26, 306–315 (1985).

The present invention is illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($C^{13}$ NMR) were measured for solutions in deuterochoroform (CDCl$_3$) or D$_6$-dimethylsulfoxide (DMSO-D$_6$) and peak positions are expressed in parts per million (ppm) downfield from tetramethylsilane (TMS). The peak shapes are denoted as follows: s, singlet; d, doublet; t, triplet; q, quartet; m, multiplet; b, broad; c, complex; h, heptet.

EXAMPLE 1

5-Amino-6-methoxyquinoline

Commercially available 6-methoxyquinoline (13.80 g) was nitrated according to the procedure of Campbell, et. al. (J. Am. Chemo Soc., 1946, 68, 1559) to give 5-nitro-6-methoxyquinoline (17.51 g). This crude product was directly reduced according to the procedure of Jacobs, et. al. (J. Am. Chem. Soc., 1920, 42, 2278) to give 5-amino-6-methoxyquinoline (6.25 g). M.p. 152.5°–154.5° C.

EXAMPLE 2

5-Amino-6-methylthioquinoline

Commercially available 6-chloroquinoline (33.3 g) was nitrated according to the procedure described in Example 1 to give 5-nitro-6-chloroquinoline (20.36 g). This material (15 g) was allowed to react with sodium methylthiolate according to the procedure of Massie (Iowa State Coll. J. Sci. 1946, 21, 41; CA 41:3044 g) to give 5-nitro-6-methylthioquinoline (13.61 g). This material (3.70 g) was reduced using iron (5.62 g) and hydrochloric acid (1.5 ml) in 50% aqueous ethanol (50 ml) to give 5-amino-6-methylthioquinoline (3.0 g). M.p. 88.5°–90.5° C.

EXAMPLE 3

3-Amino-2,4-bis(methylthio)-6-methylpyridine

To a solution of 15.5 g (0.22 mol) sodium methanethiolate in 200 ml methanol was added slowly with stirring under nitrogen a solution of 20.8 g (0.1 mol) 3-nitro-2,4-dichloro-6-methylpyridine in 150 ml methanol. A precipitate formed and the mixture was stirred overnight at room temperature. The mixture was then filtered and the solid was washed first with methanol and then with water. 3-Nitro-2,4-bis(methylthio)-6-methylpyridine (18.9 g, 82% yield) was obtained as a yellow solid, mp 172–176C.

$^1$H NMR (CDCl$_3$): δ2.45 (s, 3H); 2.51 (s, 3H); 2.55 (s, 3H); 6.77 (s, 1H).

A mixture of 18.9 g (0.082 mol) 3-nitro-2,4-bis(methylthio)-6-methylpyridine and 18.9 g Raney nickel in 600 ml. 1,4-dioxane and 300 ml methanol was shaken with hydrogen (15 psi) in a Parr hydrogenation apparatus for 3.5 hours. The catalyst was filtered and the filtrate was concentrated to dryness in vacuo. The solid residue was chromatographed on silica gel (650 g), eluting with 9:1 hexane/ethyl acetate to yield 14.0 g. (85% yield) of the title compound as an off white solid.

NMR (CDCl$_3$): δ2.42 (s, 3H); 2.44 (s, 3H); 2.59 (s, 3H); 4.02 (b, 2H); 6.72 (s, 1H).

The title compounds of Examples 4–6 were prepared according to the procedure of Example 3.

EXAMPLE 4

3-Amino-2,4-bis(methylthio)pyridine (79% yield)

$^1$H NMR (CDCl$_3$): δ2.45 (s, 3H); 2.60 (s, 3H); 4.14 (b, 2H); 6.88 (d, 1H); 7.90 (d, 1H).

EXAMPLE 5

3-Amino-2,4-bis(ethylthio)pyridine (86% yield)

$^1$H NMR (CDCl$_3$): δ1.29 (t, 3H); 1.34 (t, 3H); 2.91 (q, 3H); 3.21 (q, 3H); 4.30 (b, 2H); 6.93 (d, 1H); 7.86 (d,1H).

EXAMPLE 6

3-Amino-2,4-bis(ethylthio)-6-methylpyridine (86% yield)

$^1$H NMR (CDCl$_3$): δ1.30 (t, 3H); 1.32 (t, 3H); 2.40 (s, 3H); 2.90 (q, 2H); 3.18 (q, 2H); 4.18 (b,2H); 6.79 (s, 1H).

EXAMPLE 7

6-Chloro-4-(2-chlorophenyl)-2-methylthio-3-nitroquinoline

A solution of 2-amino-2',5-dichlorobenzophenone hydrochloride (1.6 g, 5.3 mmol) and 1,1-bis(methylthio)-2-nitroethylene (875 mg, 5.3 mmol) in 12 ml acetic acid was heated at 120° C. overnight. The reaction mixture was cooled to room temperature, 30 ml of water was added and the resulting mixture was extracted with 2×60 ml ethyl acetate. The ethyl acetate extracts were washed with 2×50 ml water, 2×50 ml saturated sodium bicarbonate solution and 50 ml brine, and then dried (anhydrous sodium sulfate), filtered and concentrated in vacuo. The residue was chromatographed on silica gel (440 g, 230–400 mesh), eluting with 85:15 hexane/ethyl acetate to yield the title compound as a yellow solid (1.65 g, 72% yield).

$^1$H NMR (300 MHz, CDCl$_3$) δ2.75 (s, 3H), 7.25 (c, 2H), 7.42 (m, 1H), 7.49 (m, 1H), 7.57 (m, 1H), 7.71 (m, 1H), 8.01 (d, 1H).

The title compounds of Examples 8 through 9B were prepared by a method similar to that described in Example 7.

EXAMPLE 8

4-(2-Chlorophenyl)-6-methyl-2-methylthio-3-nitroqinoline

74% yield. $^1$H NMR (300 MHz, CDCl$_3$) δ2.40, (s, 3H), 2.75 (s, 3H), 7.00 (s, 1H), 7.25 (m, 1H), 7.40 (m, 1H), 7.47 (m, 1H), 7.57 (m, 1H), 7.60 (m, 1H), 7.97 (d, 1H).

EXAMPLE 9

4-(2-Chlorophenyl-6-ethyl-2-methylthio-3-nitroquinoline

65% yield.

$^1$H NMR (300 MHz, CDCl$_3$) δ1.19 (t, 3H), 2.69 (q, 2H), 2.75 (s, 3H), 7.01 (d, 1H), 7.26 (m, 1H), 7.40 (m, 1H), 7.47 (m, 1H), 7.56 (m, 1H), 7.64 (m, 1H), 7.99 (d, 1H).

EXAMPLE 9A

4-(2-Chlorophenyl)-6,8-dimethyl-2-methylthio-3-nitroquinoline

8% yield.

$^1$H NMR (300 MHz, CDCl$_3$) δ2.35 (s, 3H), 2.39 (s, 3H), 2.77 (s, 3H), 6.84 (s, 1H), 7.22 (m, 1H), 7.30–7.57 (c, 4H).

EXAMPLE 9B

4-(2-Chlorophenyl)-6-isopropyl-2-methylthio-3-nitroquinoline

74% yield.

$^1$H NMR (300 MHz, CDCl$_3$) δ1.21 (d, 6H), 2.75 (s, 3H), 2.94 (m, 1H), 7.03 (s, 1H), 7.28 (m, 1H), 7.45 (m, 2H), 7.56 (m, 1H), 7.69 (m, 1H), 8.00 (d, 1H).

EXAMPLE 10

3-Amino-6-chloro-4-(2-chlorophenyl)quinoline

A mixture of Raney nickel (21 g) in 30 ml acetone was heated under reflux with mechanical stirring for 2 hours. The mixture was cooled to room temperature, allowed to settle and the acetone was removed by suction. A solution of 6-chloro-4-(2-chlorophenyl-2-methylthio-3-nitroquinoline (1.3 g, 3.6 mmol) in 25 ml hot ethanol was added and the resulting mixture was heated under reflux with mechanical stirring for 2 hours. The reaction mixture was cooled to room temperature and filtered and the filtrate was concentrated in vacuo. The residual yellow oil was chromatographed on silica gel (300 g), eluting with 8:2 dichloromethane/ethyl acetate to yield the title compound as a white solid (900 mg, 85% yield).

$^1$H NMR (300 MHz, CDCl$_3$) δ3.88 (b, 2H), 7.08 (d, 1H), 7.29 (c, 1H), 7.33 (m, 1H), 7.48 (c, 2H), 7.63 (c, 1H), 7.96 (d, 1H), 8.63 (s, 1H).

The title compounds of Examples 11 and 12 were prepared by a procedure similar to that described in Example 10.

EXAMPLE 11

3-Amino-4-(2-chlorophenyl)-6-methylquinoline

68% yield.

$^1$H NMR (300 MHz, CDCl$_3$) δ2.37 (s, 3H), 3.70 (b, 2H), 6.87 (s, 1H), 7.29 (c, 2H), 7.46 (c, 2H), 7.63 (c, 1H), 7.92 (d, 1H), 8,56 (s, 1H).

EXAMPLE 12

3-Amino-4-(2-chlorophenyl)-6-ethylquinoline

54% yield.

$^1$H NMR (300 MHz, CDCl$_3$) δ1.18 (t, 3H), 2.65 (q, 2H), 3.70 (b, 2H), 6.88 (s, 1H), 7.32 (c, 2H), 7.46 (c, 2H), 7.63 (c, 1H), 7.94 (d, 1H), 8.55 (s, 1H).

EXAMPLE 12A

3-Amino-4-(2-chloropheny)-6,8-dimethylquinoline

30% yield.

$^1$H NMR (300 MHz, CDCl$_3$) δ2.32 (s, 3H), 2.76 (s, 3H), 3.68 (b, 2H), 6.72 (s, 1H), 7.16 (s, 1H), 7.29 (q, 1H), 7.45 (q, 2H), 7.62 (q, 1H), 8.58 (s, 1H).

EXAMPLE 12B

3-Amino-4-(2-chlorophenyl)-6-isopropylquinoline

79% yield.

$^1$H NMR (300 MHz, CDCl$_3$) δ1.2 (d, 6H), 2.9 (h, 1H), 3.68 (b, 2H), 6.9 (d, 1H), 7.3–7.42 (c, 2H), 7.46 (c, 2H), 7.63 (m, 1H), 7.95 (d, 1H), 8.55 (d, 1H).

EXAMPLE 13

3-[3-{4,6-Bis(methylthio)-2-methylpyrimidin-5-yl}ureido]-6-chloro-4-[2-chlorohenyl)quinoline A solution of 3-amino-6-chloro-4-(2-chlorophenyl)quinoline (174 mg, 0.6 mmol) and 4,6-bis(methylthio)-2-methylpyrimidin-5-yl isocyanate (136 mg, 0.6 mmol) in 3 ml dimethylformamide was heated at 80° C. under nitrogen overnight. The reaction mixture was then cooled to room temperature, diluted with 30 ml ethyl acetate and filtered to remove some undissolved solid. The filtrate was washed with 2×30 ml water and 30 ml brine and then dried (anhydrous sodium sulfate), filtered and concentrated in vacuo to a solid. The solid was triturated with 20 ml 6:4 ethyl acetate/hexane and filtered, yielding the title compound as a white solid (110 mg). The filtrate was concentrated in vacuo and the residue was chromatographed on silica gel (100 g), eluting with 6:4 ethyl acetate/hexane to yield the title compound as a white solid (40 mg), total yield 150 mg(48%).

$^1$H NMR (300 MHz, DMSO-D$_6$) δ2.45 (s, 6H), 2.58 (s, 3H), 7.01 (m, 1H), 7.49 (b, 1H), 7.63–7.75 (c, 3H), 7.81 (b, 1H), 8.03 (b, 1H), 8.09 (d, 1H), 8.43 (b, 1H), 9.58 (s, 1H).

EXAMPLE 14

3-[3-{2,4-Bis(methylthio)-6-methylpyridin-3-yl}ureido-6-chloro-4-(2-chlorophenyl)quinoline A solution of 3-amino-6-chloro-4-(2-chlorophenyl)quinoline (174 mg, 0.6 mmol) and 2,4-bis(methylthio)-6-methylpyridin-3-yl isocyanate (136 mg, 0.6 mmol) in 3 ml dimethylformamide was heated at 80° C. under nitrogen overnight. The reaction mixture was then cooled to room temperature, diluted with 30 ml ethyl acetate and washed with 2×30 ml water, 30 ml brine, dried (anhydrous sodium sulfate), filtered and concentrated in vacuo. The solid residue was triturated with 10 ml 4:1 hexane/ethyl acetate and filtered to yield the title compound as a white solid (140 mg, 45% yield).

$^1$H NMR (300 MHz, DMSO-D$_6$) δ 2.41 (s, 3H), 2.46 (s, 3H), 2.52 (s, 3H), 6.90 (c, 1H), 7.00 (s, 1H), 7.50 (b, 1H), 7.68 (m, 3H), 7.83 (b, 1H), 7.94 (b, 1H), 8.09 (d, 1H), 8.33 (c, 1H), 9.63 (s, 1H).

The title compounds of Examples 15–33 were prepared by procedures similar to those described in Examples 13 and 14.

EXAMPLE 15

6-Chloro-4-(2-chlorophenyl)-3-[3-(6-methylthioquinolin-5-yl)ureido]quinoline

30% yield.

$^1$H NMR (300 MHz, DMSO-D$_6$) δ2.55 (s, 3H), 7.05 (d, 1H), 7.47–7.91 [total 8H, including 7.55 (m, 2H), 7.70 (m, 2H), 7.78 (d, 1H)], 8.00 (d, 1H), 8.10 (m, 2H), 8.77 (s, 1H), 8.84 (m, 1H), 9.59 (s, 1H).

EXAMPLE 16

3-[3-{4,6-Bis(methylthio)-2-methylpyrimidin-5-yl}ureido]-4-(2-chlorophenyl)-6-methylquinoline 23% yield.

$^1$H NMR (300 MHz, CDCl$_3$) δ2.37 (s, 3H), 2.41 (s, 6H) 2.62 (s, 3H), 5.71 (b, 1H), 6.12 (b, 1H), 6.87 (s, 1H), 7.15 (d, 1H), 7.28–7.51 (c, 4H), 8.04 (d, 1H), 9.75 (s, 1H).

EXAMPLE 17

3-[3-{2,4-Bis(methylthio)-6-methylpyridin-3-yl}ureido]-4-(2-chlorophenyl)-6-methylquinoline 29% yield.

$^1$H NMR (300 MHz, CDCl$_3$) δ2.31 (s, 3H), 2.36 (s, 3H), 2.39 (s, 3H), 2.50 (s, 3H), 5.60 (b, 1H), 6.09 (b, 1H), 6.47 (s, 1H), 6.84 (s, 1H), 7.12 (d, 1H), 7.25–7.45 (c, 4H), 8.03 (d, 1H), 9.82 (s, 1H).

EXAMPLE 18

3-[3-{2,4-Bis(methylthio)-6-methylpyridin-3-yl}ureido]-4-(2-chlorophenyl)-6-ethylquinoline 43% yield.

$^1$H NMR (300 MHz, CDCl$_3$) δ1.16 (t, 3H), 2.31 (s, 3H), 2.39 (s, 3H), 2.50 (s, 3H), 2.64 (q, 2H), 5.65 (b, 1H), 6.12 (b, 1H), 6.48 (s, 1H), 6.86 (s, 1H), 7.12 (d, 1H), 7.25–7.40 (c, 3H), 7.47 (d, 1H), 8.00 (d, 1H), 9.83 (s, 1H).

EXAMPLE 19

3-[3-{4,6-Bis(methylthio)-2-methylpyrimidin-5-yl}ureido]-4-(2-chlorophenyl)-6-ethylquinoline 36% yield.

$^1$H NMR (300 MHz, CDCl$_3$) δ1.18 (t, 3H), 2.40 (s, 6H), 2.59 (s, 3H), 2.67 (q, 2H), 6.92 (s, 1H), 7.20 (b, 1H), 7.34–7.54 (c, 6H), 8.20 (d, 1H), 9.84 (s, 1H).

EXAMPLE 20

3-[3-{2,4-Bis(methylthio)-6-methylpyridin-3-yl}ureido]-4-(2-chlorophenyl)-6-isopropylquinoline 45% yield.

$^1$H NMR (300 MHz, DMSO-D$_6$) δ1.16 (d, 6H), 2.41 (s, 3H), 2.46 (s, 3H), 2.50 (s, 3H), 2.91 (m, 1H), 6.87 (b, 2H), 7.36–7.86 (c, 6H), 7.99 (d, 1H), 8.26 (b, 1H), 9.49 (b, 1H).

EXAMPLE 21

3-[3-{2,4-Bis(methylthio)-6-methylpyridin-3-yl}ureido]-4-(2-chlorophenyl)-6,8-dimethylquinoline 8% yield.

$^1$H NMR (300 MHz, CDCl$_3$) δ2.30 (s, 6H), 2.39 (s, 3H), 2.49 (s, 3H), 2.79 (s, 3H), 5.64 (b, 1H), 6.05 (b, 1H), 6.47 (s, 1H), 6.69 (s, 1H), 7.10 (d, 1H), 7.25 (m, 2H), 7.36 (m, 2H), 9.84 (s, 1H).

EXAMPLE 22

3-[3-{4,6-Bis(methylthio)-2-methylpyrimidin-5-yl}ureido]-4-(2-chlorophenyl)-6-isopropylquinoline 45% yield.

$^1$H NMR (300 MH, DMSO-D$_6$) δ1.18 (d, 6H), 2.45 (s, 6H), 2.58 (s, 3H), 2.92 (m, 1H), 6.90 (s, 1H), 7.44 (b, 1H), 7.63 (c, 3H), 7.80 (b, 1H), 7.90 (b, 1H), 8.00 (b, 1H), 8.37 (s, 1H), 9.44 (s, 1H).

EXAMPLE 23

4-(2-Chlorophenyl)-6-ethyl-3-[3-(6-methylthioquinolin-5-yl)ureido]quinoline

37% yield.

$^1$H NMR (300 MHz, DMSO-D$_6$) δ1.17 (t, 3H), 2.55 (s, 3H), 2.66 (q, 2H), 6.90 (s, 1H), 7.42–7.86 (c, 8H), 7.98 (d, 2H), 8.06 (d, 1H), 8.70 (s, 1H), 8.84 (m, 1H), 9.43 (s, 1H).

EXAMPLE 24

4-(2-Chlorophenyl)-6-methyl-
3-[3(6-methylthioquinolin-5-yl)ureido]quinoline

35% yield.

$^1$H NMR (300 MHz, DMSO-D$_6$) δ2.37 (s, 3H), 2.55 (s, 3H), 6.89 (s, 1H), 7.40–7.85 (c, 8H), 7.96 (t, 2H), 8.06 (d, 1H), 8.70 (s, 1H), 8.84 (m, 1H), 9.42 (s, 1H).

EXAMPLE 25

4-(2-Chlorophenyl)-6-isopropyl-
3-[3-(6-methylthioquinolin-5-yl)ureido]quinoline 25% yield.

$^1$H NMR (300 MHz, CDCl$_3$) δ1.13 (d, 6H), 2.48 (s, 3H), 2.85 (m, 1H), 5.98 (b, 1H), 6.38 (b, 1H), 6.77 (s, 1H), 6.85 (c, 1H), 7.04 (c, 2H), 7.14 (m, 1H), 7.38 (c, 1H), 7.50 (m, 2H), 8.03 (m, 2H), 8.18 (d, 1H), 8.86 (b, 1H), 9.84 (s, 1H).

EXAMPLE 26

4-(2-Chlorophenyl)-6-isopropyl-
3-[3-(2,4,6-trimethylpyridin-3-yl)ureido]quinoline 8% yield.

$^1$H NMR (300 MHz, CDCl$_3$) δ1.18 (d, 6H), 2.13 (b, 3H), 2.32 (b, 3H), 2.49 (s, 3H), 2.9 (h, 1H), 6.41 (b, 1H), 6.78 (s, 1H), 6.88 (d, 1H), 7.1 (d, 1H), 7.32 (m, 1H), 7.39 (m, 2H), 7.51 (q, 1H), 8.04 (d, 1H), 9.72 (s, 1H).

EXAMPLE 27

4-(2-Chlorophenyl)-6-isopropyl-
3-[3-(2,4-dimethoxy-6-methylpyridin-
3-yl)ureido]quinoline 50% yield.

$^1$H NMR (300 MHz, CDCl$_3$) δ1.2 (d, 6H), 2.43 (s, 3H), 2.9 (h, 1H), 3.74 (s, 3H), 3.79 (s, 3H), 5.64 (s, 1H), 6.28 (s, 1H), 6.39 (s, 1H), 6.87 (d, 1H), 7.17 (q, 1H), 7.3–7.48 (c, 3H), 7.52 (q, 1H), 8.06 (d, 1H), 9.79 (s, 1H).

EXAMPLE 28

4-(2-Chlorophenyl)-6-methyl-
3-[3-(6-methoxyquinolin-5-yl)ureido]quinoline

11% yield.

$^1$H NMR (300 MHz, CDCl$_3$) δ2.32 (s, 3H), 3.91 (s, 3H), 6.0 (s, 1H), 6.17 (s, 1H), 6.75 (s, 1H), 6.84 (d, 1H), 7.04 (m, 2H), 7.15 (t, 1H), 7.38 (c, 3H), 8.0 (d, 1H), 8.07 (d, 1H), 8.21 (d, 1H), 8.80 (m, 1H), 9.88 (s, 1H).

EXAMPLE 29

6-Chloro-4-(2-chlorophenyl)-
3-[3-(6-methoxyquinolin-5-yl)ureido]quinoline

26% yield.

$^1$H NMR (300 MHz, CDCl$_3$) δ3.91 (s, 3H), 6.04 (s, 1H), 6.22 (s, 1H), 6.8 (d, 1H), 6.94–7.08 (m, 3H), 7.15 (t, 1H), 7.37 (m, 1H), 7.41 (d, 1H), 7.48 (q, 1H), 8.03 (d, 1h), 8.08 (d, 1H), 8.21 (d, 2H), 8.81 (m, 1H), 9.99 (s, 1H).

EXAMPLE 30

6-Chloro-4-(2-chlorophenyl)-
3-[3-{6-(4-methoxyphenylthio)quinolin-
5-yl}ureido]quinoline 47 % yield.

$^1$H NMR (300 MHz, CDCl$_3$) δ3.84 (s, 3H), 6.03 (b, 1H), 6.53 (b, 1H), 6.84 (b, 1H), 6.9–7.16 (c, 7H), 7.4 (c, 3H), 7.5 (q, 1H), 7.84 (d, 1H), 8.04 (d, 1H), 8.2 (d, 1H), 8.86 (m, 1H), 10.02 (s, 1H).

EXAMPLE 31

6-Chloro-4-(2-chlorophenyl)-
3-[3-(6-pentylthioquinolin-5-yl)ureido]quinoline

52% yield.

$^1$H NMR (300 MHz, CDCl$_3$) δ0.87 (t, 3H), 1.22–1.48 (c, 4H), 1.67 (m, 2H), 2.95 (t, 2H), 5.99 (b, 1H), 6.42 (b, 1H), 6.8 (d, 1H), 6.97 (d, 1H), 7.03 (d, 1H), 7.15 (t, 1H), 7.39 (q, 1H), 7.49 (q, 1H), 7.55 (d, 1H), 8.02 (q, 2H), 8.18 (d, 1H), 8.87 (q, 1H), 9.98 (s, 1H).

EXAMPLE 32

3-[3-{2,4-Bis(methylthio)-6-methylpyridin-
3-yl}ureido]-6-chloro-4-(2-chlorophenyl)-
2-methoxyquinoline 18% yield.

$^1$H NMR (300 MHz, CDC$_3$) δ2.34 (s, 3H), 2.47 (s, 3H), 2.5 (s, 3H), 4.12 (s, 3H), 6.05 (b, 1H), 6.6 (s, 1H), 7.14 (d, 1H), 7.38–7.54 (c, 6H), 7.81 (d, 1H).

EXAMPLE 33

6- Chloro-4-(2-chlorophenyl)-
2-methoxy-3-[3-(6-methylthioquinolin-
5-yl)ureido]quinoline 32% yield.

$^1$H NMR (300 MHz, CDCl$_3$) δ2.45 (s, 3H), 4.11 (s, 3H), 6.08 (b, 1H), 6.42 (b, 1H), 7.14 (d, 1H), 7.29–7.67 (c, 7H), 7.8 (d, 1H), 7.94 (b, 1H), 8.05 (d, 1H), 8.84 (m, 1H).

I claim:

1. The present invention relates to a compound of the formula

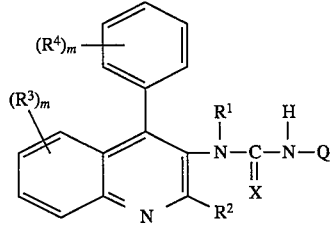

(I)

wherein each m is independently selected from 0 to 4;

R$^1$ is selected from hydrogen, (C$_1$–C$_6$) alkyl, (C$_6$–C$_{12}$) aralkyl wherein the aryl moiety is selected from phenyl, thienyl, furyl, and pyridinyl;

R$^2$ is selected from hydrogen, (C$_1$–C$_6$) alkyl and (C$_1$–C$_6$) alkoxy;

Each R$^3$ and R$^4$ is independently selected from hydrogen, halogen, (C$_1$–C$_6$) alkyl optionally substituted with one or more halogen atoms, (C$_1$–C$_6$) alkoxy optionally substituted with one or more halogen atoms, (C$_1$–C$_6$)

alkylthio optionally substituted with one or more halogen atoms, nitro, carboxyl optionally esterified with a $(C_1-C_6)$ alkyl group, hydroxyl, $(C_1-C_6)$ acyloxy and $NR^{12}R^{13}$ wherein $R^{12}$ and $R^{13}$ are the same or different and are selected from the group consisting of hydrogen, $(C_1-C_6)$alkyl, optionally halogenated $(C_1-C_6)$acyl, optionally halogenated $(C_1-C_6)$alkylsulfonyl, $(C_1-C_6)$alkylaminocarbonyl and $(C_1-C_6)$alkoxycarbonyl, or $R^{12}$ and $R^{13}$, together with the nitrogen to which they are attached, form a piperidine, pyrrolidine or morpholine ring;

X is sulfur or oxygen; and

Q is a group of the formula

XIV     XV

XVI wherein m is as defined above;

n is 0 or 1;

Each l is independently selected from 0 to 3;

Each $R^6$ and $R^7$ is independently selected from the group consisting of halogen, $(C_1-C_6)$alkyl, $(C_1-C_6)$ haloalkyl, optionally halogenated $(C_1-C_6)$ alkoxy, optionally halogenated $(C_1-C_6)$ alkylthio, $(C_5-C_7)$ cycloalkylthio, phenyl $(C_1-C_6)$alkylthio, substituted phenylthio, heteroarylthio, heteroaryloxy, $(C_1-C_6)$ alkylsulfinyl, $(C_1-C_6)$ alkylsulfonyl, $(C_5-C_7)$ cycloalkylsulfinyl, $(C_5-C_7)$ cycloalkylsulfonyl, phenyl $(C_1-C_6)$ alkylsulfinyl, phenyl $(C_1-C_6)$ alkylsulfonyl, substituted phenylsulfinyl, substituted phenylsulfonyl, heteroarylsulfinyl, heteroarylsulfonyl, and $NR^{10}R^{11}$, wherein $R^{10}$ and $R^{11}$ are the same or different and are selected from the group consisting of hydrogen, $(C_1-C_6)$ alkyl, phenyl, substituted phenyl, $(C_1-C_6)$ acyl, aroyl, and substituted aroyl, wherein said substituted phenyl and substituted aroyl groups are substituted with one or more substituents independently selected from the group consisting of $(C_1-C_6)$ alkyl, $(C_1-C_6)$ alkoxy, $(C_1-C_6)$ alkylthio, halogen and trifluoromethyl, or $R^{10}$ and $R^{11}$, together with the nitrogen to which they are attached, form a piperidine, pyrrolidine or morpholine ring; and B, D, E and G are selected from the group consisting of nitrogen and carbon, with the proviso that only one of B, D and E is nitrogen, and with the proviso that when G is nitrogen, the group XVI is attached to the nitrogen of formula I at the 4 or 5 position of the pyrimidine ring (designated by a and b) wherein any of said nitrogens may be oxidized;

or a pharmaceutically acceptable salt of such compound.

2. A compound according to claim 1, wherein Q is 6-$(C_1-C_3)$alkoxyquinolin-5-yl, 6-$(C_1-C_3)$alkylthioquinolin-5-yl, 6-$(C_1-C_3)$alkylquinolin-5-yl, 6-$(C_1-C_3)$alkylthioisoquinolin-5-yl, 6-$(C_1-C_3)$alkoxyisoquinolin-5-yl, 4,6-bis[$(C_1-C_3)$alkylthio]-2-methylpyrimidin-5-yl, 4,6-bis[$(C_1-C_3)$alkylthio]pyrimidin-5-yl, 2,4-bis[$(C_1-C_3)$alkylthio]-6-methylpyridin-3-yl or 2,4-bis[$(C_1-C_3)$alkylthio]pyridin-3-yl.

3. A compound according to claim 2, wherein $R^1$ is hydrogen and $R^2$ is as defined above and each $R^3$ and $R^4$ is selected from hydrogen, $(C_1-C_4)$alkyl, chlorine, fluorine and trifluoromethyl.

4. A compound according to claim 3 wherein $R^2$ is hydrogen.

5. A compound according to claim 3 wherein $R^2$ is $(C_1-C_6)$ alkoxy.

6. A compound according to claim 1, said compound being selected from the group consisting of:

3-[3-{4,6-Bis(methylthio)-2-methylpyrimidin-5-yl}ureido]-6-chloro-4-(2-chlorophenyl)quinoline;

3-[3-{2,4-Bis(methylthio)-6-methylpyridin-3-yl}ureido]-6-chloro-4-(2-chlorophenyl)quinoline;

6-Chloro-4-(2-chlorophenyl)-3-[3-(6-methylthioquinolin-5-yl)ureido]quinoline;

3-[3-{2,4-Bis(methylthio)-6-methylpyridin-3-yl}ureido]-4-(2-chlorophenyl)-6-methylquinoline;

3-[3-{4,6-Bis(methylthio)-2-methylpyrimidin-5-yl}ureido]-4-(2-chlorophenyl)-6-methylquinoline;

3-[3-{4,6-Bis(methylthio)-2-methylpyrimidin-5-yl}ureido]-4-(2-chlorophenyl)-6-ethylquinoline;

3-[3-{2,4-Bis(methylthio)-6-methylpyridin-3-yl}ureido]-4-(2-chlorophenyl)-6-ethylquinoline;

4-(2-Chlorophenyl)-6-methyl-3-[3-(6-methylthioquinolin-5-yl)ureido]quinoline;

4-(2-Chlorophenyl)-6-ethyl-3-[3-(6-methylthioquinolin-5-yl)ureido]quinoline;

3-[3-{2,4-Bis(methylthio)-6-methylpyridin-3-yl}ureido]-4-(2-chlorophenyl)-6-isopropylquinoline;

3-[3-{4,6-Bis(methylthio)-2-methylpyrimidin-5-yl}ureido]-4-(2-chlorophenyl)-6-isopropylquinoline;

4-(2-Chlorophenyl)-6-isopropyl-3-(6-methylthioquinolin-5-yl)ureido]quinoline; and 3-[3-{2,4-Bis(methylthio)-6-methylpyridin-3-yl}ureido]-4-(2-chlorophenyl)-6,8-dimethylquinoline;

4-(2-Chlorophenyl)-6-isopropyl-3-[3-(2,4,6-trimethylpyridin-3-yl)ureido]quinoline;

4-(2-Chlorophenyl)-6-isopropyl-3-[3-(2,4-dimethoxy-6-methylpyridin-3-yl)ureido]quinoline;

4-(2-Chlorophenyl)-6-methyl-3-[3-(6-methoxyquinolin-5-yl)ureido]quinoline;

6-Chloro-4-(2-chlorophenyl)-3-[3-(6-methoxyquinolin-5-yl)ureido]quinoline;

6-Chloro-4-(2-chlorophenyl)-3-[3-{6-(4-methoxyphenylthio)quinolin-5-yl}ureido]quinoline;

6-Chloro-4-(2-chlorophenyl)-3-[3-(6-pentylthioquinolin-5-yl)ureido]quinoline;

3-[3-{2,4-Bis(methylthio)-6-methylpyridin-3-yl}ureido]-6-chloro-4-(2-chlorophenyl)-2-methoxyquinoline;

6-Chloro-4-(2-chlorophenyl)-2-methoxy-3-[3-(6-methylthioquinolin-5-yl)ureido]quinoline.

7. A compound according to claim 1 wherein Q is 6-methoxyquinolin-5-yl, 6-methylthioquinolin-5-yl, 6-methoxyisoquinolin-5-yl, 6-methylthioisoquinolin-5-yl, 2-methyl-4,6-(bismethylthio)pyrimidin-5-yl, 6-methyl-2,4-bis(methylthio)pyridin-3-yl, 2,4-bis(ethylthio)pyridin-3-yl 2,4,6-trimethylpyridin-3-yl, 2,4-dimethoxy-6-methylpyridin-3-yl, 6-(4-methoxyphenylthio)quinolin-5-yl and 6-pentylthioquinolin-5-yl.

8. A pharmaceutical composition for inhibiting acyl coenzyme A: cholesterol acyltransferase, inhibiting intestinal absorption of cholesterol, reversing or slowing the development of atherosclerosis, or lowering the concentration of serum cholesterol in a mammal, comprising an amount of a compound according to claim 1 that is effective in inhibiting acyl coenzyme A: cholesterol acyltransferase or intestinal absorption of cholesterol, or is effective in reversing or slowing the development of atherosclerosis or lowering the concentration of serum cholesterol, and a pharmaceutically acceptable carrier.

9. A method for inhibiting acyl coenzyme A: cholesterol acyltransferase, inhibiting intestinal absorption of cholesterol, reversing or slowing the development of atherosclerosis, or lowering the concentration of serum cholesterol in a mammal, comprising an amount of a compound according to claim 1 that is effective in inhibiting acyl coenzyme A: cholesterol acyltransferase or intestinal absorption of cholesterol, or is effective in reversing or slowing the development of atherosclerosis or lowering the concentration of serum cholesterol and a pharmaceutically acceptable carrier.

10. A compound according to claim 1 comprising at least one radiolabel.

11. A compound according to claim 10, wherein said radiolabel is tritium or carbon-14.

* * * * *